United States Patent [19]

Lingwood

[11] Patent Number: 4,597,999

[45] Date of Patent: Jul. 1, 1986

[54] METHOD FOR COUPLING A HYDROCARBON CONTAINING MOLECULAR SPECIES

[75] Inventor: Clifford A. Lingwood, Toronto, Canada

[73] Assignee: The Hospital for Sick Children, Toronto, Canada

[21] Appl. No.: 657,542

[22] Filed: Oct. 4, 1984

[51] Int. Cl.$^4$ .......................... B05D 3/06; B01J 19/12
[52] U.S. Cl. ..................................... 427/54.1; 427/2; 424/32; 424/88; 204/157.6; 204/157.68; 204/157.81
[58] Field of Search ............... 204/158 R; 424/32, 88; 427/54.1, 53.1

[56] References Cited

U.S. PATENT DOCUMENTS

| | | | |
|---|---|---|---|
| 3,458,416 | 7/1969 | Hardwick et al. | 204/158 R |
| 3,849,274 | 11/1974 | Fields | 204/158 R |
| 4,342,739 | 8/1982 | Kakimi et al. | 424/32 |
| 4,411,754 | 10/1983 | Kaetsu et al. | 424/32 |

*Primary Examiner*—Howard S. Williams
*Attorney, Agent, or Firm*—Rogers, Bereskin & Parr

[57] ABSTRACT

The present invention relates to a method for covalently coupling two molecular species and to the product of such coupling. The method has particular application to the binding of hydrocarbon containing ligands to a support matrix as may be required in, for example, affinity chromatography.

15 Claims, No Drawings

METHOD FOR COUPLING A HYDROCARBON CONTAINING MOLECULAR SPECIES

BACKGROUND OF THE INVENTION

The invention relates to methods for covalently coupling two molecular species. In particular, the invention relates to a method of coupling a hydrocarbon containing molecule to another molecule or to a support matrix. Methods of this type have many applications including enzyme-linked immunosorbant assays (ELIAS), affinity chromatography, immunocongugate preparation and the preparation of immobilized enzymes.

Heterobifunctional cross-linking agents containing two or more groups subject to independent activation allow the controlled step wise coupling of one molecular target to another.

A combined thermochemical-photochemical cross-linking agent provides the required independence of activation of the two reacting groups. In addition, the photoactivable group may be selected to allow the production, under mild reaction conditions, of a very reactive intermediate with a low level of target specificity.

It is known that certain azides, when photoactivated, produce a highly reactive nitrene intermediate capable of insertion into even carbon-hydrogen bonds.

The use of a heterobifunctional cross-linking agent having a photo-activable group with a low level of target specificity, such as an azide, is particularly advantageous in the coupling of biological molecules to a support matrix.

Examples of suitable biological molecules include various drugs, digoxin, steroids, proteins, and in fact, almost any hydrocarbon containing molecule.

In most such molecules, there will be a large number of carbon sites where coupling may occur. Although coupling at some of these sites may be precluded by steric, electrostatic or other considerations, most of these sites should be available for coupling.

Methods previously used for covalently coupling two molecules often relied on coupling at a relatively few sites on the molecules, usually at functional groups. Often such coupling would affect the molecules biological or chemical activity.

In contrast to previous methods, using the present invention, coupling at any one of the large number of carbon sites on the molecule is unlikely to have any significant effect on the molecule's biological or chemical activity. Even if coupling at a few of the carbon sites would affect the molecule's activity, there are a large number of sites available for coupling and probability considerations alone dictate that most of the coupling reactions should occur at sites where there is no significant effect on the molecule's activity.

The support matrix may be any one of a large number of natural and synthetic polymers well known for such purposes including aminopropyl and aminoaryl glass and aminohexylagarose. These and other suitable supports are available commercially in the form of beads.

The use of such heterobifunctional (thermophotochemical) cross-linking agents to covalently couple two molecular species has been reported. (See "Photochemical Immobilization of Enzymes and Other Biochemicals" by Patrick Guire in Methods in Enzymology, 44 1976, and "Photochemical Coupling of Enzymes to Mammalian Cells:, by P. Guire et al, in Pharmacological Research Communications, Volume 9, No. 1, 1977).

However, the results achieved in terms of overall coupling, particularly when coupling biological molecules as ligands to a support matrix, were quite low. This is largely thought to be the result of two problems associated with the photo-activated coupling step.

Firstly, because of the high reactivity of the nitrene intermediate coupling may occur with molecules other than the target molecule including organic solvent molecules if the reaction occurs in solution.

Secondly, the target molecule must be brought close enough to the photo-activable group for coupling to occur on photo-activation of the group.

SUMMARY OF THE INVENTION

It has now been discovered that considerably increased yields, and much shorter reaction times, can be achieved by removing solvent molecules by evaporation prior to carrying out the photo-activable step.

According to the invention, a method for coupling two molecular species is provided comprising the steps of:
(a) combining
  (i) a first molecular species having a functionality reactive with hydrocarbon when photo-activated; and
  (ii) a solution of at least one, hydrocarbon containing, molecular species
  in the absence of photo-radiation to which the said functionality is sensitive;
(b) removing the solvent;
(c) irradiating the mixture with photoradiation to which said functionality is photosensitive.

A method is also provided for coupling two molecular species by means of a heterobifunctional cross-linking agent comprising the steps of:
(a) combining
  (i) a first molecular species; and
  (ii) a heterobifunctional cross-linking agent having a first functionality reactive with said first molecular species and a second functionality reactive with hydrocarbon when photo-activated;
  in the absence of photo-radiation to which said second functionality is photosensitive;
(b) adding a solution of at least one, hydrocarbon containing, molecular species, in the absence of photo-radiation to which said second functionality is sensitive;
(c) removing the solvent;
(d) irradiating the mixture with photo-radiation to which said second functionality is photosensitive.

According to another aspect of the invention, a method of preparing a first molecular species for coupling with at least one, hydrocarbon containing, molecular species is provided comprising:
(a) combining
  (i) a first molecular species; and
  (ii) a heterobifunctional cross-linking agent having a first functionality reactive with said first molecular species and a second functionality reactive with hydrocarbon when photo-activated;
  in the absence of photo-radiation to which said second functionality is photo-sensitive.

In another aspect of the invention, a support for use in affinity chromatography is provided comprising:
(a) a support matrix;
(b) at least one hydrocarbon containing species;
(c) a heterobifunctional cross-linking agent having one functionality covalently coupled to said support matrix and a second functionality covalently coupled to a carbon in said hydrocarbon-containing species.

In yet another aspect of the invention a support for use in coupling a hydrocarbon-containing species is provided comprising:
(a) a support matrix;
(b) a heterobifunctional cross-linking agent having one functionality covalently coupled to said support matrix and a second functionality reactive with hydrocarbon carbon when photoactivated.

DETAILED DESCRIPTION OF A PREFERRED EMBODIMENT

In a preferred embodiment, columns are prepared for use in affinity chromatography using a heterobifunctional cross-linking agent to covalently couple hydrocarbon containing molecules, as ligands, to a support matrix consisting of amino glass or agarose beads.

Beads suitable for use as a support matrix and having various "free" functional groups available for coupling with a cross-linking agent are readily available commercially.

Examples of support matrices containing "free" amino groups including aminopropyl and aminophenyl glass and aminohexylagarose.

The selection of a heterobifunctional cross-linking agent will depend on the support matrix used and the molecule to be coupled. Two heterobifunctional cross-linking agents suitable for coupling hydrocarbon containing molecules to a support matrix consisting of an amino glass or agarose are 4-methylazidobenzidimate (MABI) and N-hydroxysuccinimidylazidobenzoate (HSAB).

These heterobifunctional cross-linking agents will spontaneously couple in the dark to available amino groups to form an imminoester and an amide respectively.

Each of these agents also contains an azide group which, when photo-activated, produces an extremely reactive nitrene species capable of insertion into even carbon hydrogen bonds.

The use of nitrene insertion in the case of most biological molecules will result in a wide range of undefined linkage positions on the molecule. Although the spectrum of linkages may be reduced somewhat by electrostatic or other interactions, there should still be, in most cases, a large number of possible coupling sites. Probability considerations alone dictate that coupling at most of these sites will have little if any effect on the molecule's biological activity.

The high reactivity of the nitrene species will result in undesired coupling between the photo-activable group and solvent molecules if the photoactivable reaction is carried out in solution. This can be avoided by removing the solvent through evaporation.

In additon, removal of the solvent by evaporation leaves the desired ligand on the surface of the beads forming the support matrix and in close proximity to the photo-activable functionality on the heterobifunctional cross-linking agent.

The preparation of a support matrix for use in affinity chromatography may be carried out in step wise fashion.

The support matrix, which may comprise an amino glass for example, and the heterobifunctional cross-linking agent, which may be one of 4-methylazidobenzidimate (MABI) or N-hydroxysuccinimidylazidobenzoate (HSAB) for example, are first mixed together in the dark resulting in spontaneous coupling of the two to form an "activated" support matrix. The desired ligand is then added to the "activated" support matrix in the dark. After removal of the solvent by evaporation, the mixture is irradiated for a few minutes with light of a suitable wave length for activation of the photo-activable group. This results in the coupling of the desired ligand to the support matrix.

The support matrix so prepared can then be used in the preparation of columns for affinity chromatography in conventional fashion.

It will be appreciated that a support matrix having free groups other than amino may be used and the heterobifunctional cross-linking agent would be selected accordingly. For example, a support matrix comprising a thiol glass might be used in conjunction with a thiol reactive heterobifunctional cross-linking agent.

In some instances, it may be desirable to be able to release bound ligands. In such cases, the heterobifunctional cross-linking agent selected may also contain a cleavable functionality. Examples of such cleavable functionalities include the disulphide and azo groups, both of which may be cleaved under mild reaction conditions.

It will also be appreciated, that the "activated" support matrix prepared by reacting the heterobifunctional cross-linking agent and support matrix need not be used immediately, but may be stored in the dark.

The method of the invention may also be used to prepare a support matrix having a mixture of two or more species coupled as ligands. This is done by preparing a solution containing a mixture of the desired ligands and then proceeding in the same manner as for a single ligand.

The use of a two-ligand system may be useful, for example, in preparing a column for isolating an enzyme catalyzing a bisubstrate system. The two substrates are bound as ligands to a support matrix using the method of the invention, which support matrix can then be used to prepare a column for affinity chromatography.

Although the preparation of a support matrix for affinity chromatography has been described, other applications for the method of the invention, involving the coupling of two molecular species, will occur to the skilled worker. Examples of such applications, but not by way of limitation, include enzyme-linked immunosorbant assays (ELIAS), immunoconjugate preparation and the preparation of immobilized enzymes. Such applications may require the coupling of biological molecules to various insoluble matrices. For example, ferritin or latex beads in immunocongugate preparation.

Having generally described this invention, a further understanding can be obtained by reference to certain specific examples which are provided herein for puposes of illustration and are not intended to be limiting unless otherwise specified.

EXAMPLES

Abbreviations Used in Examples

Sulfatoxylgalactosylacylalkylglycerol—SGG
Galactosylacylalkylglycerol—GG
Galactosyl ceramide—GC
3'phosphoadenosine 5'phosphosulfate—PAPS
Uridine 5'diphosphate Nacetylglucosamine—UDP$^{14}$C-GLcNAc
Phosphate buffered saline—PBS
4-Methylazidobenzidimate—MABI
N-hydroxysuccinimidylazidobenzoate—HSAB
3'5'Adenosine diphosphate—3'5' ADP

EXAMPLE 1

Amino glass beads, as shown in Table 1, were shaken in 1 ml methanol/water 1:1 containing HSAB diluted from 100 mM stock in dimethylsulfoxide, for 1 hr. at room temperature in the dark. The beads were washed once with water. SGG was dissolved in 1 ml ethanol and added. The beads were rotoevaporated to dryness in the dark. Photo-labelled beads with absorbed glycolipid were irradiated 1 cm from mineral light II at 260 nm for 2 min. with stirring. The beads were then washed six times with: (a) 5 ml ethanol,; (b) 5 ml methanol/chloroform 1:1, (c) 5 ml chloroform/methanol 2:1. The wash factions were pooled, evaporated and redissolved in 1 ml ethanol. An aliquot was removed and compared to the original material by galactose dehydrogenase assay after acid hydrolysis. No SGG binding to control amino glass beads treated with 10% benzaldehyde was observed.

TABLE 1

| | % Coupling |
|---|---|
| (1) Aminopropylglass (100 mg) 2 mM HSAB | |
| 1. 0.1 mg SGG | 15.0 |
| 2. 0.2 mg SGG | 71.0 |
| 3. 0.4 mg SGG | 40.0 |
| (2) Aminophenylglass (100 mg) 0.4 mg SGG | |
| 1. 1 mM HSAB | 20 |
| 2. 2 mM HSAB | 35 |
| 3. 4 mM HSAB | 39 |
| (3) Aminohexyl-agarose (0.5 ml)$^+$ 0.4 mg SGG | |
| 1. 1 mg/ml MABI$^{++}$ | 53 |
| 2. 2 mg/ml MABI | 42 |
| 3. 3 mg/ml MABI | 60 |

$^+$The chloroform/methanol 2:1 (v/v) wash omitted for amino agarose supports.
$^{++}$MABI binding to amino matrix was carried out in water. Equal aliquots of MABI were added to 0, 20 and 40 min. to give the final concentration indicated. Other conditions were as described for HSAB.

EXAMPLE 2

Affinity chromatography columns with amino glass support matrices as set out in Table 2 were prepared in accordance with the procedure of Example 1 using the concentrations of cross-linking agents as set out in Table 2.

TABLE 2

Affinity Columns Prepared by Photoactivated Cross-Linking

| LIGAND | CROSSLINKING | SUPPORT | % COVALENT COUPLING | IMMOBILIZED LIGAND DENSITY ($\mu$mole/ml) |
|---|---|---|---|---|
| SGG(0.2 mg) 2 mM | HSAB | NH$_2$propyl-glass | 71 | 0.34 |
| SGG(0.4 mg) 1 mg/ml | MABI | NH$_2$propyl-glass | 39 | 0.3 |
| SGG(3.5 mg) | MABI | NH$_2$—agarose | 46 | 1.23 |
| GG(2.0 mg) | HSAB | NH$_2$—agarose | 70 | 0.87 |
| GC(0.4 mg) | HSAB | NH$_2$phenyl-glass | 73 | 0.73 |
| *PAP$^{35}$S(2.5 mg) | HSAB | NH$_2$—agarose | 94 | 1.5 |
| *UDP$^{14}$C—GLcNAc (0.5 mg) | HSAB | NH$_2$—agarose | 91 | 0.93 |
| *UDP$^{14}$C—GLcNAc (0.5 mg) | HSAB | NH$_2$ propyl-glass | 54 | 0.83 |
| $^3$H—Digoxin (1.5 mg) | HSAB | NH$_2$—agarose | 26 | 0.17 |
| $^3$H—Digoxin (1.5 mg) | HSAB | NH$_2$ phenyl-glass | 21 | 0.15 |

Glycolipid columns were prepared as described in Table 1. *Hydrophilic ligands were dissolved in water prior to adsorption into activated matrix. After photocoupling, the columns were washed extensively with water (50–100 ml). The wash fraction was lyophilized and redissolved in water and remaining radio-lable was compared to the original material prior to coupling. An aliquot of the matrix was also removed to determine bound radioactivity. The value for the coupling efficiency shown is calculated from the former data since the latter is difficult to quantitate.

EXAMPLE 3

To five grams CPG-aminoaryl glass beads (Pierce Chemical Co.) in 40 ml. of methanol was added 800 microliters of a 100 mM solution of HSAB (Pierce Chemical Co.) dissolved in dimethylsulfoxide to give a 2 mM final concentration of HSAB.

The mixture is shaken rapidly for one hour at 37° C. During this period, the flask is covered with aluminum foil so as to exclude light.

The methanol is then decanted. The glass beads are then washed with a further 50 ml. of methanol by shaking at 37° C. for 10 minutes.

A solution of 50 mg. of testosterone (Sigma Chemical Co.) in 50 ml. of methanol is prepared. The glass beads are then transferred to a round bottom flask to which is added the solution of testosterone. The solvent is then evaporated off in a rotary evaporator, and the final traces of solvent are removed under high vacuum.

The glass beads are then poured onto a plastic dish and irradiated with a handheld short wavelength uv light for two hours, the dish being shaken intermittently.

The beads are then washed with 50 ml. of methanol for one hour at 37° C. with shaking. The methanol is poured into a flask and the washing procedure is repeated. The two methanol washes are combined and the uv absorbance measured. In this fashion, the amount of testosterone remaining in the methanol can be calculated and acordingly the amount bound to the glass beads.

The glass beads are then dried under vacuum and stored until used.

EXAMPLE 4

A double ligand "mixed matrix" affinity column was prepared in the following fashion. 2 ml.aminohexylagarose was added to 8 ml. MeOH/H$_2$O 1:1 (v/v). HSAB was added to form a 2 mM solution and the mixture was shaken in the dark at room temperature for one hour. The beads were centrifuged and washed once with water. 4 mg. SGG was then dissolved in 4 ml. of EtOH. 4 mg. of 3'5' adenosine diphosphate (3'5' ADP) is then dissolved in 1 ml. of water. The beads were resuspended in 5 ml. of water. The 3'5' ADP and the SGG were added and the mixture rotorevaporated in the dark. The beads were then irradiated and washed in a column with 80 ml. Ethanol/H$_2$O 1:1. The wash was reconstituted to 2 ml. Ethanol/H$_2$O 1:1. 10 microliters were then compared by thin layer chromatography to 20 microliters of the original SGG solution and 5 microliters of the 3'5'ADP solution. The result was then visualized by orcinol spray for carbohydrate.

Covalent binding was estimated to be greater than 75% for SGG and greater than 90% for 3'5'ADP.

I claim:

1. A method of covalently coupling two molecular species comprising:
   (a) combining
      (i) a first molecular species having a functionality reactive with hydrocarbon when photo-activated; and
      (ii) a solution of at least one, hydrocarbon containing, molecular species
      in the absence of photo-radiation to which said functionality is sensitive;
   (b) removing the solvent;
   (c) irradiating the mixture with photo-radiation to which said functionality is photosensitive.

2. The method of claim 1 wherein the first molecular species is a support matrix.

3. The method of claim 2 wherein the support matrix is comprised of beads.

4. The method of claim 1, 2 or 3 wherein the functionality reactive with hydrocarbon when photo-activated is an azide group.

5. A method of covalently coupling two molecular species comprising:
   (a) combining
      (i) a first molecular species; and
      (ii) a heterobifunctional cross-linking agent having a first functionality reactive with said first molecular species and a second functionality reactive with hydrocarbon when photo-activated;
      in the absence of photo-radiation to which said second functionality is photosensitive;
   (b) adding a solution containing at least one, hydrocarbon containing, molecular species, in the absence of photo-radiation to which said second functionality is sensitive;
   (c) removing the solvent;
   (d) irradiating the mixture with photo-radiation to which said second functionality is photosensitive.

6. The method of claim 5 wherein the first molecular species is a support matrix.

7. The method of claim 6 wherein the support matrix is comprised of beads.

8. The method of claim 6 wherein the second functionality reactive with hydrocarbon when photo-activated is an azide group.

9. The method of claim 8 wherein the support matrix contains at least one functional group selected from the group consisting of amino and thiol and the first functionality on said heterobifunctional cross-linking agent is reactive with said functional group.

10. The method of claim 8 wherein the heterobifunctional cross-linking agent further contains a cleavable functionality.

11. The method of claim 10 wherein the cleavable functionality is selected from the group consisting of azo and disulfide.

12. The method of claim 6 wherein the support matrix contains at least one amino group and the heterobifunctional cross-linking agent is selected from the group consisting of 4-methylazidobenzimidate and N-hydroxysuccinimidylazidobenzoate.

13. The method of claim 5 or 6 wherein the first molecular species contains attached thereto a functional group selected from the group consisting of amino and thiol and the first functionality on said heterobifunctional cross-linking agent is reative with said functional group.

14. The method of claim 5 or 6 wherein the heterobifunctional cross-linking agent further contains a cleavable functionality.

15. The method of claim 5 or 6 wherein the heterobifunctional cross-linking agent further contains a cleavable functionality selected from the group consisting of azo and disulfide.

* * * * *